United States Patent [19] [11] 4,143,064
Loeffler et al. [45] Mar. 6, 1979

[54] MANUFACTURE OF β-HALOCETALS OR β-HALOKETALS

[75] Inventors: Hans-Peter Loeffler, Ludwigshafen; Karl Kiehs, Lampertheim, both of Fed. Rep. of Germany

[73] Assignee: BASF Aktiengesellschaft, Ludwigshafen, Fed. Rep. of Germany

[21] Appl. No.: 782,638

[22] Filed: Mar. 30, 1977

[30] Foreign Application Priority Data

May 8, 1976 [DE] Fed. Rep. of Germany ....... 2620498

[51] Int. Cl.² .................... C07C 139/00; C07C 41/06; C07C 67/00
[52] U.S. Cl. ........................... 260/456 R; 260/456 P; 260/463; 560/132; 560/133; 560/137; 560/138; 560/140; 560/144; 560/145; 568/592
[58] Field of Search .......... 260/613 D, 613 R, 456 R, 260/456 P, 463; 560/133, 132, 137, 138, 140, 144, 145

[56] References Cited

U.S. PATENT DOCUMENTS 2,000,252 5/1935 Reppe et al. ................ 260/613 D X
2,550,637 4/1951 Copenhaver ................ 260/613 D X Primary Examiner—Bernard Helfin
Attorney, Agent, or Firm—Keil & Witherspoon

[57] ABSTRACT

A process for the manufacture of β-haloacetals or β-haloketals by reaction of substituted or unsubstituted phenols with vinyl ethers in the presence of chlorine-liberating compounds and an inert diluent or solvent at a temperature of from −70 to +40° C.

3 Claims, No Drawings

MANUFACTURE OF β-HALOCETALS OR β-HALOKETALS

The present invention relates to a process for the manufacture of β-haloacetals or β-haloketals by reaction of substituted or unsubstituted phenols with vinyl ethers in the presence of chlorine-liberating compounds.

It is known to prepare β-haloacetals or β-haloketals by reaction of 1,2-dihaloalkyl ethers with alcohols or phenols in the presence of a hydrogen halide acceptor (Houben-Weyl, Methoden der organischen Chemie, 6/3, 255, Georg Thieme-Verlag, Stuttgart, 1965).

1,2-dihaloalkyl ethers belong as alkylation agents to a series of chemically related substances such as α, α'-dichlorodimethyl ether and α-chloromethylmethyl ether. Because of the carcinogenicity of these compounds (Chemie in unserer Zeit, 9, 79–84, 1975; Chem. Soc. Reviews, 4, 289, 1975), special precautionary measures have to be employed when handling them (General Industry, Standards and Interpretations, Vol. I, February 1974, part 1910.93, United States Department of Labor, Occupational Safety and Health Administration, Office of Standards). Processes based on a reaction with halogenated alkyl ethers cannot therefore be operated for occupational medicine reasons, or only at considerable expense on a commercial scale.

We have now found a process for the manufacture of β-haloacetals or β-haloketals of the formula

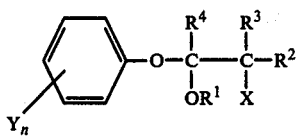

where $R^1$ denotes linear or branched alkyl of 1 to 6 carbon atoms, or phenyl which may be substituted by halogen or linear or branched alkyl of a maximum of 4 carbon atoms, $R^2$ and $R^3$ denote hydrogen; linear or branched alkyl of 1 to 4 carbon atoms; phenyl which may be substituted by halogen or linear or branched alkyl; or halogen, $R^2$ and $R^3$ not simultaneously denoting halogen, $R^4$ denotes hydrogen; linear or branched alkyl of 1 to 4 carbon atoms; or phenyl which may be substituted by halogen or linear or branched alkyl, X denotes halogen, Y denotes the radical $-O-SO_m-R^5$, $R^5$ denoting linear or branched alkyl or haloalkyl, each of 1 to 4 carbon atoms, or phenyl which may be substituted by linear or branched alkyl of 1 to 4 carbon atoms or by halogen, and m denoting one of the integers 1 and 2, Y further denotes the radical

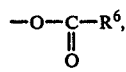

$R^6$ denoting linear or branched alkyl, alkoxy or haloalkyl, each of 1 to 4 carbon atoms, or alkylamino or dialkylamino of 1 to 4 carbon atoms in one alkyl group, and n denotes one of the integers 0, 1, 2 and 3, wherein phenols of the formula

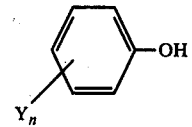

where Y and n have the above meanings, are reacted with vinyl ethers of the formula

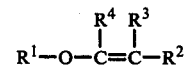

where $R^1$, $R^2$, $R^3$ and $R^4$ have the above meanings, and a positive chlorine-liberating compound in the presence of an inert diluent or solvent at a temperature of from −70° to +40° C.

That the reaction would take the course it does is surprising, as undesirable reactions were to be expected in view of the state of the art in the reaction of the invention. Thus, it is known that phenols are chlorinated in the phenyl nucleus at temperatures as low as room temperature by tert.-butyl hypochlorite (Chem. Rev., 54, 925, 1954). Further, the vinyl ether, as an electron-rich olefin, would have been expected to polymerize under the conditions of the reaction according to the invention (Russ. Chem. Reviews, 30, 207, 1961).

It is an essential advantage of the process that carcinogenic haloalkyl ethers are not used, thus obviating the need for costly technology and safety measures.

Suitable chlorine-liberating compounds are those which provide positive chlorine, for instance tert.-butyl hypochlorite and N-chlorosuccinimide. They are expediently added to the phenol in excess; a molar ratio of chlorine-liberating compound to phenol of from 1.05:1 to 1.5:1 is advantageous.

The reaction temperature may be varied within wide limits; generally, the reaction is carried out at a temperature of from −70° to +40° C., preferably from −50° to +10° C., and at atmospheric or superatmospheric pressure. In general, the reaction pressure is conditioned by the total vapor pressure of the components at the reaction temperature.

The reaction may be carried out in solution or suspension. Suitable diluents or solvents are those which are inert to the reactants under the reaction conditions, for example ethers such as dioxane, tetrahydrofuran and 1,2-dimethoxyethane; nitriles such as acetonitrile; and esters such as ethyl acetate and butyl acetate. Mixtures of these solvents may also be employed.

The tert.-butanol formed during the reaction with tert.-butyl hypochlorite may be recovered.

It is advantageous to add small amounts of bases or inhibitors to the reaction mixture in order to prevent polymerization of the vinyl ether or a direct reaction of the vinyl ether with the phenol without the participation of the chlorine-liberating compound. To preclude these side-reactions, 0.5 to 5 mole %, based on phenol, of sodium bicarbonate, triethylamine or potassium carbonate may for instance be added.

The vinyl ethers of the formula III used as starting compounds are known from the literature and can be easily produced industrially (cf., for example, Ann., 601, 98, 1956). They may be reacted in a molar ratio or in an up to 10-fold molar excess with the phenols. The molar ratio of vinyl ether to phenol is preferably 1.2 to 4:1.

Suitable substituents for $R^1$ in the formulae I and III are linear or branched alkyl, e.g., methyl, ethyl, n-propyl, isopropyl, dibutyl, pentyl and hexyl, and unsubstituted or halogen- or alkyl-substituted phenyl, e.g., 4-chlorophenyl, 2,4-dichlorophenyl, 4-bromophenyl, 4-methylphenyl, 4-ethylphenyl, 3,5-dimethylphenyl and 4-isopropylphenyl.

$R^2$, $R^3$ and $R^4$ may denote hydrogen, alkyl such as methyl, ethyl, n-propyl, isopropyl and butyl, and unsubstituted or halogen- or alkyl-substituted phenyl, e.g., the phenyl radicals listed at $R^1$. $R^2$ and $R^3$ may also denote halogen, preferably chlorine or bromine.

X in the formulae I and III stands for halogen, e.g., fluorine, chlorine and bromine, especially chlorine.

The phenyl nucleus in the formulae I and II may be unsubstituted or bear up to three substituents. Examples of suitable substituents for Y in the formulae I and II are sulfur-containing radicals of the formula $-O-SO_m-R^5$, where $R^5$ denotes alkyl, for instance methyl, ethyl, propyl and butyl; haloalkyl, for instance fluoromethyl, chloromethyl, bromomethyl, α-chloroethyl, β-chloroethyl, and 3-chloropropyl; or unsubstituted or halogen- or alkyl-substituted phenyl, for example the phenyl radicals listed at $R^1$, and m denotes one of the integers 1 and 2; other substituents for Y are carboxylic acid radicals of the formula

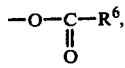

where $R^6$ denotes alkyl, for instance methyl, ethyl, propyl and butyl; haloalkyl, for instance chloromethyl, trifluoromethyl, trichloromethyl, β-chloroethyl and β-bromoethyl; alkoxy, for instance methoxy, ethoxy, propoxy, isopropoxy and butoxy; alkylamino, for instance methylamino, ethylamino, propylamino and butylamino; and dialkylamino, for instance dimethylamino, diethylamino, methylethylamino, di-n-propylamino and ethylpropylamino.

The β-haloacetals and β-haloketals obtainable by the process of the invention are valuable intermediates for the manufacture of insecticidal active ingredients (U.S. Pat. No. 3,962,316).

The following examples illustrate the process of the invention.

EXAMPLE 1

Preparation of 1-methoxy-1-phenoxy-2-chloroethane

At −20° C., 10 parts by weight of vinyl methyl ether is added all at once to 4.5 parts by weight of phenol in 50 parts by weight of tetrahydrofuran. Over a period of 30 minutes and at −20° C., 10 parts of tert.-butyl hypochlorite (Org. Synthesis, Coll. Vol. IV, 125, John Wiley & Sons, Inc., New York/London, 1963) is dripped into this mixture. The resultant mixture is allowed to come to room temperature. After stirring for 2 hours at room temperature, the solvent is removed, and distillation gives 5 parts by weight of 1-methoxy-1-phenoxy-2-chloroethane, b.p. 89°–91° C./4mm Hg.

EXAMPLE 2

Preparation of o-(1-methoxy)-2-chloroethoxyphenyl-N-methyl carbamate 89 parts by weight of pyrocatechol mono-N-methyl carbamate (J. prakt. Chem., 313, 626, 1971) in 500 parts by weight of tetrahydrofuran is cooled to −20° C. Over a period of 30 minutes at −20° C., 81 parts by weight of vinyl methyl ether is gassed into this solution and 110 parts by weight of tert.-butyl hypochlorite is simultaneously dripped in. The mixture is then stirred for 30 minutes at −20° C. and for 30 minutes at 0° C. The solvent is removed, and volatile impurities are removed from the residue at 30° C./0.1 mm Hg. 50 parts by weight of toluene and 30 parts by weight of petroleum ether are then added. Suction filtration gives 100 parts by weight of a crystalline product. The pure substance, m.p. 78°–80° C., is obtained by recrystallization from ether.

EXAMPLE 3

Preparation of o-(1-methoxy)-2-chloroethoxyphenyl-N-methyl carbamate

At 0° C., 23.2 parts by weight of vinyl methyl ether is gassed into a mixture of 11.7 parts by weight of pyrocatechol mono-N-methyl carbamate, 50 parts by weight of tetrahydrofuran and 13.3 parts by weight of N-chlorosuccinimide (Helv. chim. Acta, 36, 1768, 1953). The mixture is stirred for 2 hours at 20° C., and the solution is concentrated and chromatographed using silica gel.

The desired product, m.p. 71°–74° C., is obtained.

We claim:

1. A process for the manufacture of β-haloacetals or β-haloketals of the formula

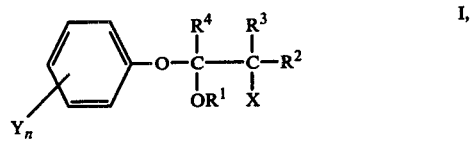

where $R^1$ denotes linear or branched alkyl of 1 to 6 carbon atoms, or phenyl which may be substituted by halogen or linear or branched alkyl of a maximum of 4 carbon atoms; $R^2$ and $R^3$ denote hydrogen, linear or branched alkyl of 1 to 4 carbon atoms, phenyl which may be substituted by halogen or linear or branched alkyl, or halogen, with the proviso that $R^2$ and $R^3$ cannot simultaneously denote halogen; $R^4$ denotes hydrogen, linear or branched alkyl of 1 to 4 carbon atoms, or phenyl which may be substituted by halogen or linear or branched alkyl; X denotes chlorine; Y denotes the radical $-O-SO_m-R^5$; $R^5$ denoting linear or branched alkyl or haloalkyl, each of 1 to 4 carbon atoms, or phenyl which may be substituted by linear or branched alkyl of 1 to 4 carbon atoms or by halogen, and m denoting one of the integers 1 and 2, Y further denotes the radical

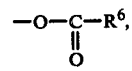

$R^6$ denoting linear or branched alkyl, alkoxy or haloalkyl, each of 1 to 4 carbon atoms, or alkylamino or dialkylamino of 1 to 4 carbon atoms in one alkyl group, and n denotes one of the integers 0, 1, 2 and 3, which process comprises reacting phenols of the formula

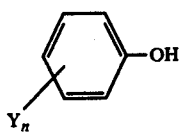

where Y and n have the above meanings, with vinyl ethers of the formula

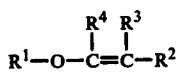

where $R^1$, $R^2$, $R^3$ and $R^4$ have the above meanings, and with a positive chlorine-liberating compound selected from the group consisting of tert.-butyl hypochlorite and N-chlorosuccinimide in the presence of an inert diluent or solvent at a temperature of from $-50°$ to $+10°$ C.

2. A process as set forth in claim 1, wherein the molar ratio of phenol to vinyl ether is from 1:1.2 to 1:4.

3. A process as set forth in claim 1, wherein the reaction is carried out with tert.-butyl hypochlorite as the chlorine-liberating compound.

* * * * *